United States Patent [19]

Kotaka et al.

[11] 4,194,118
[45] Mar. 18, 1980

[54] DETECTOR FOR USE IN INFRARED GAS ANALYZER

[75] Inventors: Mitsuo Kotaka; Hirotoshi Ishikawa; Kaisuke Muraki; Ryo Takahashi; Tamizo Matsuura, all of Musashino, Japan

[73] Assignee: Yokogawa Electric Works, Ltd., Tokyo, Japan

[21] Appl. No.: 888,408

[22] Filed: Mar. 20, 1978

[30] Foreign Application Priority Data

Mar. 30, 1977 [JP] Japan .................................. 52/38864
Apr. 1, 1977 [JP] Japan .................................. 52/40383
Sep. 19, 1977 [JP] Japan .................................. 52/125773

[51] Int. Cl.² .............................................. G01J 1/00
[52] U.S. Cl. ........................................ 250/343; 250/352
[58] Field of Search ............... 250/352, 343, 338, 345, 250/353; 356/51

[56] References Cited

U.S. PATENT DOCUMENTS

| 2,844,729 | 7/1958 | Winterling et al. | 250/345 |
| 3,539,804 | 11/1970 | Billetdeaux et al. | 250/343 |
| 3,860,344 | 1/1975 | Garfunkel | 250/345 |
| 4,041,314 | 8/1977 | Oppelt | 250/338 |

FOREIGN PATENT DOCUMENTS

44-31319 of 1969 Japan ....................... 250/352

*Primary Examiner*—Alfred E. Smith
*Assistant Examiner*—Carolyn E. Fields
*Attorney, Agent, or Firm*—Parmelee, Johnson, Bollinger & Bramblett

[57] ABSTRACT

A metallic block has a conical measuring-light inlet port and a conical reference-light inlet port formed therein. The ports intersect at a light sensor. The inlet ports are closed by respective multilayer interference filters. Temperature control means, which may be responsive to the light sensor output, maintains the metallic block, and thus the filters and sensor, at a fixed temperature.

2 Claims, 5 Drawing Figures

DETECTOR FOR USE IN INFRARED GAS ANALYZER

CROSS REFERENCE TO A RELATED APPLICATION

The commonly assigned and copending U.S. Patent Application Ser. No. 888223 by Kotako et al entitled Infrared Gas Analyzer.

BACKGROUND OF THE INVENTION

The present invention relates to a detector for use in an infrared gas analyzer for analyzing components in a gas by utilizing absorption of infrared rays, and more particularly to an improved detector employing an infrared-sensing semiconductor element as a light sensor and also a multilayer interference filter.

Heretofore, it has been customary in the conventional infrared gas analyzer to have multilayer interference filters disposed substantially adjacent to a reference cell and a sample cell. The dimensions of the filters are selected to be equal to the area of windows in the cells in order to transmit a sufficient amount of infrared rays. Moreover, since the multilayer interference filter has a temperature coefficient, it is necessary to maintain the filters at a fixed temperature in a high-sensitivity infrared gas analyzer. Consequently the known apparatus is equipped with some suitable means to meet the stable temperature requirement. On the other hand, the infrared-sensing semiconductor element also needs to be kept free from the influence of ambient temperature fluctuation during use, thus it is necessary to provide means to maintain constant the temperature of the infrared-sensing element. Accordingly, the following disadvantages are present in the conventional apparatus: (1) The influence of ambient temperature fluctuation is avoided by providing a temperature control means for each of the multilayer interference filters and the infrared-sensing semiconductor element, or by incorporating the multilayer interference filters and the infrared-sensing semiconductor element in a thermostatic oven. This inevitably renders the infrared gas analyzer structure complicated and expensive.

(2) Since a multilayer interference filter is dimensionally large (substantially equal to the area of a window in the cell), its thermal capacity is great and makes temperature control difficult.

The present invention has been accomplished in an attempt to eliminate the above disadvantages, and an object of the invention is to provide an improved detector for use in an infrared gas analyzer capable of easily achieving temperature control for both the infrared-sensing semiconductor element and the multilayer interference filter.

SUMMARY OF THE INVENTION

In accordance with the invention in one of its aspects a light sensor is disposed in light inlet ports formed in a metallic block, and multilayer filters are provided to close the light inlet ports. The temperatures of both the light sensor and the multilayer filters are controllable simultaneously.

According to the invention in another of its aspects a reference-light inlet port and a measuring-light inlet port are formed individually in a single metallic block.

According to another aspect of the invention each of the light inlet ports is conical.

And according to yet another aspect of the invention the a-c component of a signal obtained by irradiating intermittent reference light and measuring light to the light sensor is used as a measurement signal, and the signal composed of the superposed a-c and d-c components is fed as an input to the temperature control means.

DESCRIPTION OF PREFERRED EMBODIMENTS

Figure 1:
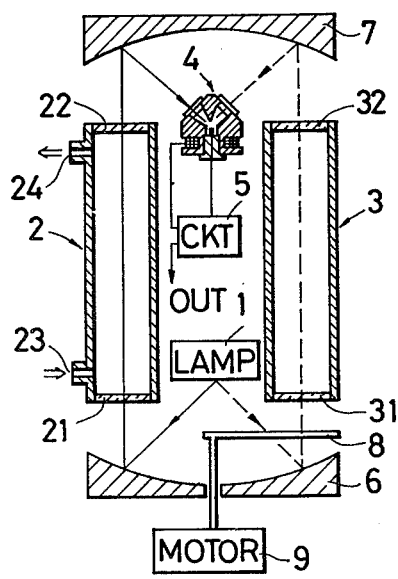
FIG. 1 is a sectional view of an infrared gas analyzer equipped with a detector embodying the present invention.
Figure 2:
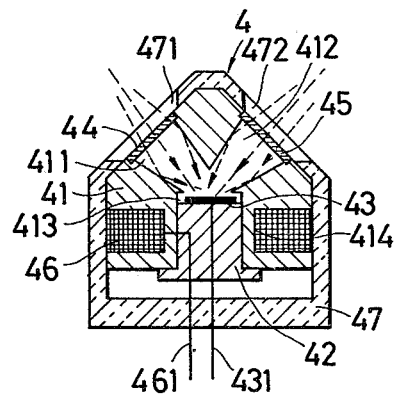
FIG. 2 is a sectional view of an embodiment of the invention.
Figure 3:
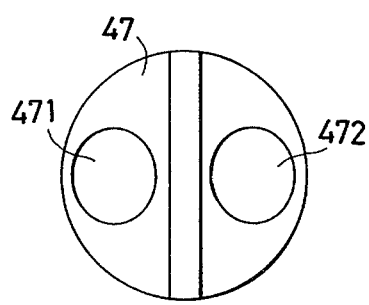
FIG. 3 is a plan view of the embodiment illustrated in FIG. 2.

An infrared gas analyzer equipped with a detector of this invention is shown in FIG. 1. As for the detector, FIGS. 2 and 3 illustrate its structure in more detail. In FIG. 1, a gas analyzer includes an infrared-ray source 1 and a sample cell 2 filled with a sample gas. The sample cell 2 has an inlet port 23 and an outlet port 24 for introducing and exhausting the sample gas. A reference cell 3 encloses a pure nitrogen gas therein and has windows 31, 32 for transmission of infrared rays. (The analyzer of FIG. 1 is designed for measurement of components co-existing with nitrogen.) A detector 4 is located in the vicinity of the focal point of a concave reflex mirror 7 to receive intermittent light passed through the reference cell 3 and the sample cell 2. The light emitted from the infrared-ray source 1 is first formed into parallel rays by a concave reflex mirror 6 and then the parallel rays are passed through an interrupter 8 rotated by a motor 9.

Now a further detailed explanation of the detector 4 and the signal converter/temperature controller 5 will be given with reference to FIGS. 2 through 4.

FIG. 2 is a sectional view of the detector 4 illustrating the structure thereof, and FIG. 3 is its plan view. A metallic block 41 has a conical measuring-light inlet port 411 and a conical reference-light inlet port 412 for admitting the measuring light and the reference light respectively. A light-sensor mounting hole 413 is formed at the intersection of the light inlet ports 411, 412 of the metallic block 41. A base plate 42 is inserted and fixed in the mounting hole 413 of the metallic block 41, and a light sensing element 43 as a thermistor-bolometer is secured onto the base plate 42. A wire 431 serves to connect the light sensing element 43 to the signal converter/temperature controller 5. A multilayer interference filter 44 is attached to the metallic block 41 to close the measuring-light inlet port 411, and another multilayer interference filter 45 is also attached to the metallic block 41 to close the reference-light inlet port 412. Each of the interference filters is so positioned as to face the incoming light related thereto. The space formed by the light inlet ports 411, 412 and the mounting hole 413 is maintained in a completely hermetic state and is filled with nitrogen gas $N_2$. A heater 46 is disposed in an annular groove 414 in the outer surface of block 41 so as to heat the metallic block 41. A connecting wire 461 feeds the output of the signal converter/temperature controller 5 to the heater 46. The entire metallic block 41 is coated with a member 47 composed of, for example, bakelite resin. Owing to the coating member 47, the metallic block 41 is effectively shielded from ambient temperature. A window 471 is provided for the measuring-light inlet port 411, and a window 472 is provided for the reference-light inlet port 412.

Figure 4:
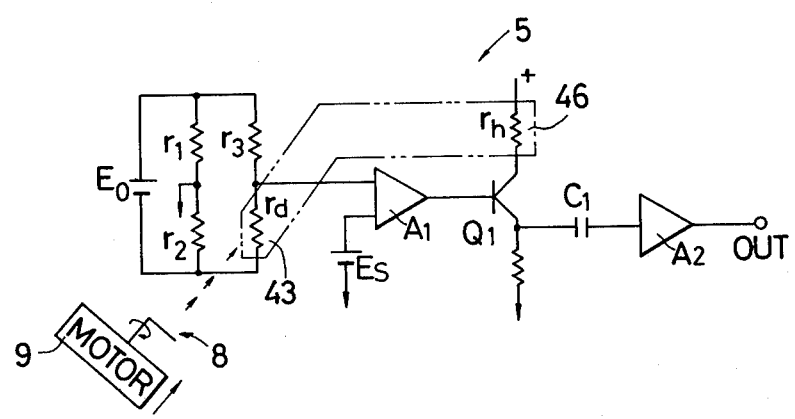
FIG. 4 is a circuit diagram of a signal converter/temperature controller in the analyzer of FIG. 1.

In the circuit configuration of signal converter/temperature controller 5 shown in FIG. 4, the thermistor-bolometer 43 is represented by $r_d$ is regarded as a resistance element. This element is combined with other resistance elements r1, r2, r3, stable to temperature, and a d-c power source Eo to constitute a bridge circuit which receives the measuring light and the reference light intermitted by the interrupter 8. The difference between the unbalanced voltage of the bridge circuit and a preset voltage Es is amplified by a low-noise amplifier A1 of high input impedance and is further amplified by a transistor Q1, the output current of which energizes the heater 46 (resistance element $r_h$). Simultaneously, the a-c component of the output current is fed alone through a capacitor C1 to an amplifier A2 so that a measurement signal is obtained from the output terminal OUT thereof.

The infrared gas analyzer with the above described detector performs as follows. The light emitted from the infrared-ray source 1 is intermitted by the interrupter 8 and is alternately transmitted through the sample cell 2 and the reference cell 3. The intermittent light is then condensed by the concave reflex mirror 7 and is introduced to the detector 4. The light thus introduced passes through the multilayer interference filters 44, 45 at a right angle of incidence to the surfaces thereof and impinges on the thermistor-bolometer 43. The right angle of incidence is ideal in comparison with oblique incidence of the light upon the filter surface, because there occurs neither a reduction of sensitivity resulting from reflection from the multilayer interference filter nor a variation in the transmission band which generally tends to be widened by oblique incidence.

The conversion efficiency of the thermistor-bolometer 43 indicates its maximum value when the reflecting surface of the concave reflex mirror 7 is ideal and the thermistor-bolometer 43 is located at the focal point of the mirror 7. However, even if those conditions are not satisfied completely, the conversion efficiency can be enhanced due to the conical shape and the smooth finished surfaces of the light inlet ports 411, 412. According to experiments conducted by the inventors, the conversion efficiency actually attained was more than twice the efficiency with the known cylindrical port.

The operation of the signal converter/temperature controller 5 is as follows. The resistance $r_d$ of thermistor-bolometer 43 is dependent on the intermittent light obtained by the interrupter 8 and also on the heating temperature of heater 46. The former indicates a-c changes of a short period, while the latter indicates d-c changes with a slow response due to a large time constant of the heater. Accordingly, the output signal of the bridge circuit consisting of the resistance elements rd, r1, r2, r3 and the power source Eo is the d-c component and the a-c component superposed thereon. The d-c component is a signal representing the temperature of the thermistor-bolometer 43, and the a-c component can be regarded as a measurement signal corresponding to the gas component contained in the sample gas. The output signal of the bridge circuit and a preset signal Es are applied differentially to the amplifier A1, whose output is further amplified by the transistor Q1 to produce a signal for energizing the heater 46. On the other hand, the a-c component alone is amplified by the amplifier A2 through the capacitor C1 to become a measurement signal. Even when the a-c component is contained in the heater energizing signal, it causes substantially no harmful influence on the control system since the time constant of the heater 46 is great, and thus the thermistor-bolometer 43 can be kept at a temperature corresponding to the preset voltage Es. As the signal converter/temperature controller 5 functions to control the temperature of the metallic block 42 in the detector 4, it follows that the thermistor-bolometer 43 and the multilayer interference filters 44, 45 installed in the metallic block 42 can be maintained at the same temperature.

Figure 5:
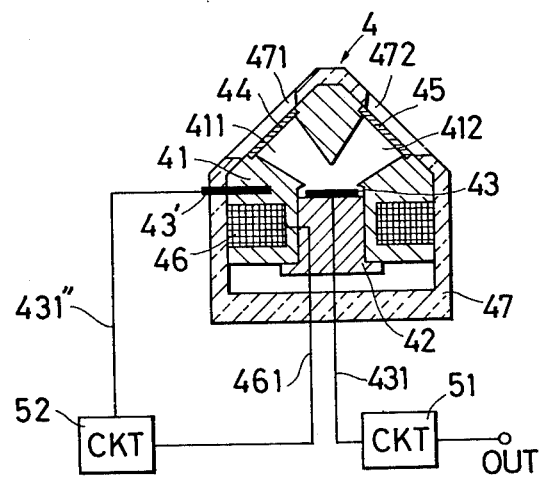
FIG. 5 is a sectional view of another embodiment of the invention.

The structure of another embodiment of the present invention is illustrated in FIG. 5; the reference numerals and symbols equal to those in FIG. 2 denote the same elements and an explanation for them is omitted here. The difference between the two embodiments of FIGS. 2 and 5 is in the circuit configuration of a temperature control system for the metallic block 41 of the detector 4. In FIG. 5, a temperature detecting element 43' is embedded in a portion of the metallic block 41, and a temperature controller 52, connected to detecting element 43' by wire 431", is provided separately from a signal converter 51. In this configuration, it is possible to use known circuits to form the signal converter 51 and the temperature controller 52.

It is to be understood that the present invention is not limited to the foregoing example in which the thermistor-bolometer is used as a light sensing element and is heated. It may be replaced with, for example, a photo-conductive cell such as T1S, PbS, CdS or the like, and the structure may be so modified as to cool such element. One of cooling means available is a low-temperature stabilizer equipped with a Peltier-effect element.

According to the detector of this invention, as described in detail hereinabove, the temperatures of multi-layer interference filters and an infrared-sensing semiconductor element installed in a metallic block are stabilized by controlling the metallic block to maintain a fixed temperature. Therefore, a single temperature control system is sufficient to meet the requirement, thereby simplifying the structure of the analyzer. Moreover, since the multilayer interference filters are disposed at the light inlet ports in the metallic block, the detector can be shaped in smaller dimensions as compared with the conventional one where the filters are attached in the vicinity of windows of a sample cell and a reference cell. The smaller detector has a reduced thermal capacity to facilitate temperature control. Furthermore, miniaturizing the multilayer interference filters brings about an economic advantage.

We claim:
1. A detector for use in an infrared gas analyzer wherein one light beam is passed through a sample cell and a second light beam is passed through a reference cell, to produce two resultant beams to be sensed comparatively, apparatus comprising:
   a metallic block formed with first and second cone-shaped light inlet ports which intersect within said block;
   a light sensing element secured to said block at the intersection of said two ports;

multilayer interference filters secured to said block and covering the entrances to said light inlet ports, said filters being positioned to be at right angles to incoming light beams;

temperature control means including first circuit means coupled to said light sensing element and responsive to variations in temperature thereof to regulate the temperature of said metallic block to tend to maintain a constant block temperature; and signal detecting means including second circuit means coupled to said light sensing element and responsive to variations in light impinging thereon to produce a corresponding measurement signal;

whereby a measurement signal relating to the density of the gas in said sample cell may be obtained by alternately directing said two resultant beams to said two light ports respectively.

2. The detector as in claim 1, wherein said light sensing element comprises a resistor which varies with received light and temperature;

resistance means coupled to said light sensing element resistor to form a bridge circuit;

a d-c power source coupled to said bridge circuit;

means coupling the output of said bridge circuit to said first circuit means to effect temperature regulation in accordance with changes in the bridge output caused by changes in temperature of said light sensing element; and a-c coupling means coupling the output of said bridge circuit to said second circuit means to produce a measurement signal in accordance with the a-c bridge signal component resulting from the alternating impingement of said two resultant beams on said light sensing element.

* * * * *